United States Patent
Iwamoto et al.

(10) Patent No.: US 10,953,057 B2
(45) Date of Patent: Mar. 23, 2021

(54) FUNCTIONAL FEED

(71) Applicants: IDEMITSU KOSAN CO., LTD., Tokyo (JP); KYORITSU SEIYAKU CORPORATION, Tokyo (JP)

(72) Inventors: Eiji Iwamoto, Chiyoda-ku (JP); Yuji Shizuno, Chiyoda-ku (JP); Yasuhiro Suzuki, Sendai (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 503 days.

(21) Appl. No.: 15/547,238

(22) PCT Filed: Jan. 29, 2016

(86) PCT No.: PCT/JP2016/052752
§ 371 (c)(1),
(2) Date: Jul. 28, 2017

(87) PCT Pub. No.: WO2016/121963
PCT Pub. Date: Aug. 4, 2016

(65) Prior Publication Data
US 2018/0021393 A1    Jan. 25, 2018

(30) Foreign Application Priority Data
Jan. 30, 2015 (JP) .................. 2015-017572

(51) Int. Cl.
*A61K 36/22* (2006.01)
*A61K 31/05* (2006.01)
*A61K 31/192* (2006.01)
*A23K 20/00* (2016.01)
*A23K 50/75* (2016.01)
*A61K 9/00* (2006.01)

(52) U.S. Cl.
CPC ............. *A61K 36/22* (2013.01); *A23K 20/00* (2016.05); *A23K 50/75* (2016.05); *A61K 9/0056* (2013.01); *A61K 31/05* (2013.01); *A61K 31/192* (2013.01); *Y02P 60/87* (2015.11)

(58) Field of Classification Search
None
See application file for complete search history.

(56) References Cited

U.S. PATENT DOCUMENTS

| 5,725,894 A | 3/1998 | Toyomizu et al. |
| 6,379,694 B1 | 4/2002 | Hatano et al. |
| 2011/0250303 A1* | 10/2011 | Nagashima ............ A61K 31/05 424/769 |
| 2012/0077884 A1 | 3/2012 | Mochizuki et al. |
| 2013/0224320 A1* | 8/2013 | Campmany ............ A61K 31/05 424/776 |

FOREIGN PATENT DOCUMENTS

| EP | 1 103 190 A1 | 5/2011 |
| JP | 8-231410 A | 9/1996 |
| JP | 2001-151675 A | 6/2001 |
| JP | 2006-316048 A | 11/2006 |
| JP | 2010-75079 A | 4/2010 |
| JP | 2014-121331 A | 7/2014 |
| WO | 2010/143627 A1 | 12/2010 |
| WO | WO 2011/152533 A1 | 12/2011 |

OTHER PUBLICATIONS

Faitarone et al. (2008) Brazilian Journal of Poultry Science, vol. 10, No. 1, pp. 53-57. (Year: 2008).*
Braz et al. (2019) South African Journal of Animal Science 49 (No. 3): 513-521. (Year: 2019).*
Lopez et al. (2012) Arq. Bras. Med. Vet. Zootec., 64, n.4, 1027-1035. (Year: 2012).*
International Search Report dated Apr. 26, 2016, in PCT/JP2016/052752, filed Jan. 29, 2016.
Japan Livestock Technology Association, the Third Egg-Laying Chicken Subcommittee in the Fiscal Year 2007, Document No. 4, "The Result of the Survey on Actual Situation in the Farming and Management of Egg-Laying Hens", 2007, <URL:jlta.lin.gr.jp/report/animalwelfare/h19/hen/no3/m4_hen.pdf>, 20 pages with partial English translation.
Extended European Search Report dated Jul. 2, 2018 in European Patent Application No. 16743566.8. 8 pages.
Swain, B.K., et al., "Effect of Feeding Cashew Apple Waste and Cashew Nut Shell on the Performance of Japanese Quail Layers", Indian Journal of Animal Nutrition, XP 009506050, vol. 24-2, pp. 92-94.
Vidal, T. F., et al., "Egg Quality and Yolk Lipid Composition of Laying Hens Fed Diets Containing Cashew Nut Meal", *Food Science and Technology*, XP 055484199, vol. 33 No. 1, Feb. 25, 2013, pp. 172-179.
Swain, B.K., et al., "Use of Agro-Industrial By-Products to Economise Feed Cost in Poultry Production", Technical Bulletin. Retrieved from the Internet: URL: http://www.ccari.res.in/TB%20No.13.pdf, XP 55484066, Jan. 1, 2008, No. 13, pp. 1-10 with cover pages.

* cited by examiner

*Primary Examiner* — Russell G Fiebig
(74) *Attorney, Agent, or Firm* — Oblon, McClelland, Maier & Neustadt, L.L.P.

(57) ABSTRACT

The present invention provides an egg-laying rate-improving agent for egg-laying hens, quails, or broiler breeders, the egg-laying rate-improving agent being characterized by comprising unheated cashew nut shell liquid, heated cashew nut shell liquid, anacardic acid, cardanol, and/or cardol.

7 Claims, No Drawings

FUNCTIONAL FEED

TECHNICAL FIELD

The present invention relates to an egg-laying rate-improving agent for egg-laying hens, quails, or broiler breeders, which comprises unheated cashew nut shell liquid, heated cashew nut shell liquid, anacardic acid, cardanol, and/or cardol, as well as to a feed and an egg production method for egg-laying hens, quails, or broiler breeders using the same.

BACKGROUND ART

Egg-laying hens (layers) receive not only nutritional care and disease management but also photoperiodic treatment and the like with an aim to allow egg collection once a day and eventually to increase their productivity. However, decrease in egg-laying rate and/or reduction in the quality of eggs, particularly in egg shell strength, are increasingly observed with aging, suggesting that the productivity of hens is inevitably reduced based on their physiology. There have been techniques using the physiology of hens for the purpose of improving the egg-laying rate and the quality of eggs through a fasting or low-nutrition treatment, such as forced molting and induced molting; however, several problems due to limited nutrition have been identified, including increase in death rate (mortality rate), deterioration in immune function, extremely slow recovery of egg-laying rate due to the nutrient restriction, and the like.

Non-Patent Document 1 describes in Section "(5) Induced molting methods and egg-laying rates derived therefrom" that an egg-laying rate of more than 85% in egg-laying hens after molting was achieved by about 30% of farmers and an egg-laying rate of not more than 90% in egg-laying hens after molting as achieved by only about 10% of the farmers even though the low-nutritional diet switching, in which a type of feed that causes a lower mortality rate as compared with other molting methods is continuously provided, was used. Moreover, Non-Patent Document 1 describes in Section "(6) Induced molting methods and mortality rates derived therefrom" that the mortality rate in egg-laying hens after molting was on average not less than 5.6% and a mortality rate of more than 3% covered 80% of the farmers even though the low-nutritional diet switching was used.

There have been cases where functional substances, including antioxidants, probiotics (*Lactobacillus* spp., *Bacillus subtilis*), alkaloids (for example, piperine), herbs (for example, allspice, clove) and monosaccharides, are fed to hens, in addition to improving the nutritional care, to solve the above-described problems; however, there still remains in the art a need for substances to increase the productivity further.

Patent Document 1 (JP H08-231410 A) describes a coccidiosis-relieving agent for poultry including chickens for meat, such as broiler chicken, the coccidiosis-relieving agent being characterized by comprising cashew nut shell liquid and/or anacardic acids as active ingredients/an active ingredient.

Patent Document 2 (JP2001-151675A) describes a feed for poultry including chickens for meat, such as broiler chicken, to prevent and/or treat coccidiosis, the feed being characterized by comprising as active ingredients cashew nut oil and/or anacardic acids as well as at least one selected from an organozinc compound, betaine and a *Bacillus* bacterium.

However, it was unknown that the provision of cashew nut shell liquid enabled egg-laying hens, quails, or broiler breeders to improve their egg-laying rate and egg-laying hens to decrease the death rate during molting.

PRIOR ART DOCUMENTS

Patent Documents

Patent Document 1: JP H08-231410A
Patent Document 2: JP2001-151675A

Non-Patent Document

Non-Patent Document 1: In the homepage of the Japan Livestock Technology Association, Reviewing Committee on the Livestock Farming and Management in view of Animal Welfare, the Third Egg-Laying Chicken Subcommittee in the Fiscal Year 2007, Document No. 4, The Result of the Survey on Actual Situation in the Farming and Management of Egg-Laying Hens: Internet <URL: jlta.lin.gr.jp/report/animalwelfare/h19/hen/no3/m4_hen.pdf>.

SUMMARY OF THE INVENTION

Objects of the present invention are to increase the egg-laying rate, to decrease the death rate during forced molting or induced molting, and to increase the egg-laying rate after molting, in egg-laying hens, quails, or broiler breeders. That is, the present invention aims to increase the productivity (egg production) in egg-laying hens, quails, or broiler breeders.

The inventors intensively studied to solve the above-described problems and found that use of unheated cashew nut shell liquid, heated cashew nut shell liquid, anacardic acid, cardanol, and/or cardol had effects on the increase of egg-laying rate, the decrease of death rate during forced molting or induced molting, and the increase of egg-laying rate after molting, in egg-laying hens. Thereby, the inventors have completed the present invention.

That is, the present invention is as follows.
(1) An egg-laying rate-improving agent for egg-laying hens, quails, or broiler breeders, comprising unheated cashew nut shell liquid, heated cashew nut shell liquid, anacardic acid, cardanol, and/or cardol.
(2) The egg-laying rate-improving agent according to (1), wherein the number of dead hens per week during the egg-laying phase is less than 0.1% of the number of introduced young hens.
(3) The egg-laying rate-improving agent according to (1) or (2), wherein the egg-laying hens are subjected to forced molting or induced molting.
(4) The egg-laying rate-improving agent according to (3), wherein the death rate during the molting process is not more than 2%.
(5) The egg-laying rate-improving agent according to any of (1) to (4), wherein the egg-laying rate is maintained at 90% for 90 days or longer.
(6) A feed comprising the egg-laying rate-improving agent according to any of (1) to (5).
(7) The egg-laying rate-improving agent according to any of (1) to (6), wherein layer performance is enhanced by increasing or maintaining the quality of eggs.
(8) The feed according to (7), wherein unheated cashew nut shell liquid, heated cashew nut shell liquid, anacardic acid, cardanol, and/or cardol is present in the feed at a concentration of 0.0001 to 10% by mass.

(9) A method of increasing an egg-laying rate, the method comprising providing egg-laying hens, quails, or broiler breeders with the feed according to (7) or (8).
(10) The method of increasing the egg-laying rate according to (9), wherein the egg-laying hens are subjected to forced molting or induced molting.
(11) A method for egg production, the method comprising providing egg-laying hens, quails, or broiler breeders with the feed according to (7) or (8).
(12) Unheated cashew nut shell liquid, heated cashew nut shell liquid, anacardic acid, cardanol, and/or cardol for use in enhancement of egg production in egg-laying hens, quails, or broiler breeders.
(13) Use of unheated cashew nut shell liquid, heated cashew nut shell liquid, anacardic acid, cardanol, and/or cardol in the manufacture of the egg-laying rate-improving agent for egg-laying hens, quails, or broiler breeders.

Effect of the Invention

Use of the egg-laying rate-improving agent of the present invention for egg-laying hens, quails, or broiler breeders, or use of a feed comprising the same can increase the egg-laying rate and the persistency of egg production in egg-laying hens, quails, or broiler breeders. Moreover, the egg-laying rate-improving agent of the present invention for egg-laying hens or the feed comprising the same can be used to decrease the death rate of egg-laying chickens during induced molting or forced molting.

DETAILED DESCRIPTION OF THE INVENTION

The egg-laying rate-improving agent of the present invention comprises unheated cashew nut shell liquid, heated cashew nut shell liquid, anacardic acid, cardanol, and/or cardol.

Cashew nut shell liquid is an oily liquid contained in the nutshell of the cashew nut tree (*Anacardium occidentale* L.). Cashew nut shell liquid contains, as its components, anacardic acid, cardanol and cardol. In general, anacardic acid is converted into cardanol by heat treatment. Cashew nut shell liquid (unheated) extracted by pressing cashew nut shells comprises 55 to 80% by mass of anacardic acid, 5 to 20% by mass of cardanol and 5 to 30% by mass of cardol, as described in J. Agric. Food Chem. 2001, 49, 2548-2551. Heat treatment of cashew nut shell liquid at a temperature of not lower than 70° C., preferably not lower than 130° C., causes anacardic acid, a main component of cashew nut shell liquid, to be decarboxylated and converted into cardanol and the obtained heated cashew nut shell liquid comprises 0 to 10% by mass of anacardic acid, 55 to 80% by mass of cardanol and 5 to 30% by mass of cardol. Storage of cashew nut shell liquid at room temperature (20° C.) for about one year or longer may cause anacardic acid, a main component of cashew nut shell liquid, to be decarboxylated and converted into cardanol; and in this case, the obtained cashew nut shell liquid comprises 0 to 40% by mass of anacardic acid, 30 to 80% by mass of cardanol and 5 to 30% by mass of cardol.

Cashew nut shell liquid can be obtained as a vegetable oil extracted by pressing cashew nut shells. Moreover, cashew nut shell liquid can also be obtained by extraction, such as for example solvent extraction, of cashew nut shells. Furthermore, cashew nut shell liquid can be obtained by, for example, a solvent extraction method, which is a method as described in Patent Document 1 (JP H08-231410A). In addition, cashew nut shell liquid may refer to cashew nut shells and/or cashew nut testa obtained by pulverizing/crushing cashew nut shells, both of which comprise cashew nut shell liquid. The cashew nut testa represents the thin skin between the shell and the germ (nut) of a cashew nut. Moreover, a commercial product of cashew nut shell liquid may be used. A heated cashew nut shell liquid of the present invention can be obtained by heating cashew nut shell liquid (unheated) obtained as described above at a temperature of not lower than 70° C. and preferably not lower than 130° C. Alternatively, the cashew nut shell liquid may be a cashew nut shell liquid obtained by storage at room temperature (20° C.) for about one year or longer. The heated cashew nut shell liquid of the present invention may refer to heated nut shells and/or heated cashew nut testa obtained by pulverizing/crushing heated cashew nut shells, both of which comprise cashew nut shell liquid. In poultry (chicken and the like), the provision of some antibiotics or feeds may induce symptoms from side effects, such as decreased digestibility, diarrhea, loss of appetite and the like, and sometimes lead to death. However, the unheated cashew nut shell liquid and heated cashew nut shell liquid according to the present invention have no side-effect problems.

The content of cashew nut shell liquid in the egg-laying rate-improving agent of the present invention is preferably from 0.001% to 100% by mass, more preferably from 0.01% to 90% by mass and most preferably from 0.1% to 80% by mass. In cases where the content is not less than 0.001% by mass, a given amount of the agent can exert the effects to improve the egg-laying rate, to improve the persistency of egg production and to decrease the death rate. The content of the egg-laying rate-improving agent in the feed additive of the present invention is preferably from 0.01% to 100% by mass, more preferably from 0.05% to 100% by mass and most preferably from 0.1% to 100% by mass. The content of the feed additive in the feed of the present invention is preferably from 0.005% to 20% by mass, more preferably from 0.01% to 20% by mass and further preferably from 0.05% to 20% by mass.

When the egg-laying rate-improving agent of the present invention is contained in a feed for use, the content of cashew nut shell liquid in the feed should be from 0.0001% to 10.0% by mass, preferably from 0.0001% to 5.0% by mass, more preferably from 0.0001% to 3.0% by mass, further preferably from 0.0001% to 2.0% by mass and especially preferably from 0.0001% to 0.1% by mass, from 0.0001% to 0.05% by mass or from 0.0001% to 0.01% by mass. In cases where the content is not less than 0.0001% by mass, a given amount of the feed can exert the effects to improve the egg-laying rate, to improve the persistency of egg production and to decrease the death rate; and a content of not more than 10.0% by mass will not affect the composition of the feed, so that a content in that range is preferable. In respect of cashew nut shell liquid used in the present invention, whether cashew nut shells containing oily substances may be used directly or after pulverizing/crushing the shells, or cashew nut testa may be used, the content of cashew nut shell liquid in the egg-laying rate-improving agent, the feed additive, or the feed should fall within the above-described range in terms of the contained cashew nut shell liquid (CNSL) (CNSL is contained in cashew nut shell in a range of 25 to 30% by mass, while CNSL is contained in cashew nut testa in a range of 0.5 to 3.0% by mass).

The egg-laying rate-improving agent of the present invention may comprise anacardic acid, cardanol, or cardol, instead of cashew nut shell liquid.

Examples of anacardic acid used in the present invention include naturally-occurring anacardic acid, synthetic anacardic acid, and derivatives thereof. Moreover, a commercial product of anacardic acid may also be used. Anacardic acid can be obtained as described in Patent Document 1 (JP H08-231410A) by extracting cashew nut oil from cashew nut shells treated with an organic solvent, subjecting the obtained cashew nut oil to, for example, silica gel column chromatography, and applying a mixture of n-hexane, ethyl acetate and acetic acid with a varying ratio to the chromatography for the elution of the obtained cashew nut oil (see JP H03-240721A, JP H03-240716A, etc.). The anacardic acid as described above may be contained in the egg-laying rate-improving agent, the feed additive, or the feed in the same amount as the cashew nut shell liquid.

Examples of cardanol used in the present invention include naturally-occurring cardanol, synthetic cardanol, and derivatives thereof. Moreover, the cardanol used in the present invention can be obtained by decarboxylation of anacardic acid, a main component of cashew nut shell liquid. The cardanol as described above may be contained in the egg-laying rate-improving agent, the feed additive, or the feed in the same amount as the cashew nut shell liquid.

Examples of cardol used in the present invention include naturally-occurring cardol, synthetic cardol, and derivatives thereof. Moreover, the cardol used in the present invention can also be obtained from purification of cashew nut shell liquid. The cardol as described above may be contained in the egg-laying rate-improving agent, the feed additive, or the feed in the same amount as the cashew nut shell liquid.

Examples of animals targeted by the egg-laying rate-improving agent of the present invention include egg-laying hens or quails, or broiler breeders involved in the production of commercial chickens for meat. Furthermore, original species of these fowls may also be included.

The egg-laying hens may not only include original species and breeder species of egg-laying hens breeds but also be commercial chicken breeds, crossbreeds and improved breeds produced by breeding of those egg-laying chicken breeds. Examples of the egg-laying hens include chickens of White Leghorn, ISA Brown, Dekalb-Warren Sex-Sal-Link, Harvard-Comet, Shaver Star Cross 579, Black Minorca, Barred Plymouth Rock, White Plymouth Rock, Rhode Island Red, New Hampshire, Araucana, Silky Fowl, Polish, Nagoya-Cochin, Hinai-Jidori, Boris Brown, Julia, Julia-Lite, Babcock B400, Sonia, Maria, Laura, Novogen White, Novogen Brown, Elbe, Sakura, Momiji, and the like, and may also include crossbreeds and improved breeds thereof.

Examples of the chickens for meat include chickens of White Cornish, White Plymouth Rock, Barred Plymouth Rock, Rhode Island Red, New Hampshire, UK Chunky, US Chunky, Cobb, Avian, Arbor Acres, Hinai-Jidori, Satsuma-Jidori, Nagoya, and the like; however, examples of the chickens for meat are not limited to those breeds described above, as long as those chickens are provided for the collection of eggs to produce commercial chickens.

Preferred chicken breeds targeted by the egg-laying rate-improving agent of the present invention are, among those described above, Julia, Julia-Lite, Babcock 13400, Novogen White, Novogen Brown and Sonia.

Examples of the egg-laying quails include White Quail, Red Quail, King Quail, California Quail, Stripe-faced Wood Quail, Spot-winged Wood Quail, Long-tailed Wood Partridge, Mountain Quail, Northern Bobwhite, Grey Partridge, Montezuma Quail, Ocellated Quail, Scaled Quail, Common Quail, Yucatan Bobwhite, Crested Bobwhite, Gambel's Quail, Elegant Quail, Long-tailed Wood Partridge, Marbled Wood Quail, and Spotted Wood Quail.

The egg-laying hens targeted by the egg-laying rate-improving agent of the present invention are more preferably egg-laying hens which are subjected to forced molting or induced molting, but the rearing method is not limited to any particular form. Moreover, egg-laying hens free of coccidiosis are preferable. Unheated cashew nut shell liquid, heated cashew nut shell liquid, anacardic acid, cardanol, and/or cardol may be provided at any point in time between hatching and 36 months of age. Preferably, that time point is between hatching and 18 months of age, which is common in commercial hens, and in cases where a non-laying period is included, it is between hatching and 21 months of age, but the age of hens is not limited to the above-described age in months as long as it meets each poultry farmer's rearing conditions. Moreover, one approach seeks to increase the quality of eggs and the egg-laying rate by providing a non-laying period (forced molting or induced molting) because hens start egg production at the age of primiparity (150 to 160 days of age) and the quality of eggs starts decreasing around the age of 10 months. In the approach, the time period from 14 to 16 months of age is a guide for starting the non-laying period and, thus, the egg-laying rate-improving agent of the present invention is preferably provided in this time period. Namely, the egg-laying rate-improving agent of the present invention is preferably provided around the peak egg-laying phase and during molting process. When induced molting is implemented by low-nutritional diet switching, the egg-laying rate-improving agent mixed with a low-nutritional diet is preferably provided. The low-nutritional diet is characterized by being a low energy-low protein diet and further aims to keep the survival rate while promoting molting by reducing the amount and frequency of diet provided to these hens.

The egg-laying rate-improving agent of the present invention is preferably provided to quails during the period from hatching to 23 months of age, but the age of quails is not limited to the above-described age in months as long as those quails are provided for the collection of eggs.

The egg-laying rate-improving agent of the present invention is preferably provided to egg-laying hens, quails, or broiler breeders, for example, to increase the survival rate and the egg-laying rate, to improve the cumulative feed conversion rate, or to achieve a weight loss rate relative to the body weight before the molting process in the range of −25 to −35%, which is the reference rate for the process, as compared with the non-feeding control without provision of unheated cashew nut shell liquid, heated cashew nut shell liquid, anacardic acid, cardanol, and/or cardol. A weight loss of −25 to −30% is further preferable. As the weight loss rate approaches to a rate of −30%, while a pause in egg production is induced, the death rate (mortality rate) during the molting process is decreased and, preferably, the egg-laying rate is maintained at 90% for 90 days or longer after molting, or the death rate during the molting process is decreased to a rate of not higher than 2%. Moreover, the egg-laying rate-improving agent of the present invention provided to egg-laying hens increases the egg-laying rate and decreases the death rate and, thus, is expected to improve the quality of eggs (for example, to suppress excessive enlargement of eggs and consequent reduction in egg shell strength due to aging of chickens), to reduce the length of non-laying period after the molting process, and to improve the feed conversion rate, and so on. That is, the egg-laying rate-improving agent of the present invention can increase the duration in days of egg collection phase and contribute to increase in the productivity of egg-laying hens, quails, or broiler breeders.

In the present invention, the term "egg-laying rate" refers to a numerical value representing the ratio of the number of chickens or quails in a group that are actually laying eggs to the total number of hens or quails in the group. In an example of a simple calculation method for the egg-laying rate, for example, a case where 90 eggs are produced per day by 100 hens corresponds to an egg-laying rate of 90%. Moreover, examples of the egg-laying rate include those called "hen-house egg production" and "hen-day egg production," in which the weekly age or period of primiparity, and the decrease in number of hens due to withdrawal of spent hens are taken into consideration. The term "hen-house egg production" refers to a numerical value representing the egg-laying rate of chickens in a period of 52 weeks, the egg-laying rate being calculated by dividing the number of eggs, which have been produced by the chickens in the period from the age of 20 weeks to the age of 72 weeks (an egg-laying phase of 365 days), by the number of the chickens at the starting point (at the age of 20 weeks). The term "hen-day egg production" refers to a numerical value representing the egg-laying rate of chickens in a period of 52 weeks, the egg-laying rate being calculated by dividing the number of eggs, which have been produced by the hens in the period from the age of 20 weeks to the age of 72 weeks (an egg-laying phase of 365 days), by the number of remaining hens (the number obtained by subtracting the number of withdrawn spent hens).

In the present invention, the phrase "to improve the quality of eggs" refers to, for example, decreasing the ratio of abnormal eggs, maintaining proper egg weight, increasing the egg shell strength, and to increase the I-laugh unit. Abnormal eggs refer to double-yolked eggs, broken eggs, shell-less eggs, and eggs with blood spots. The proper egg weight varies depending on the breed of hens and is generally 40 to 76 g (in size from SS to LL) in the case of Julia-Lite. The egg shell strength relates to the egg shell thickness and the frequency of broken eggs. The general value of the egg shell strength varies depending on the breed of chickens and is on average around 3.00 to 4.30 $kg/cm^2$ in the case of Julia-Lite. The "Haugh unit" (one of the indices that represent the freshness of chicken eggs) is typically around 80 to 100 in the case of Julia-Lite.

In the present invention, the "feed conversion rate" is obtained as below from the ingested amount of animal feed required to gain a unit production in weight:

Feed conversion rate=Ingested amount of animal feed (g)/Production in weight (g).

In the present invention, the "maintenance of the egg collection phase" means seizing the peak of egg production in hens and maintaining the subsequent egg-laying rate at a high level in order to maximize the egg collection efficiency. Although the duration in days aimed by the "maintenance of the egg collection phase" varies depending on the breed of hens and rearing conditions, in the case of Julia-Lite, an indication of profitability is provided by the length of time, in days, in which an egg-laying rate of not lower than 90% is maintained. In the present invention, the "maintenance of the egg collection phase" means, for example, an egg-laying rate of 85%, preferably of not lower than 90%, maintained for 60 days or longer, preferably for 90 days or longer.

The dosage form for the egg-laying rate-improving agent of the present invention is not particularly limited, but it may be in any form, such as powder, pellet, granule, liquid, solid, tablet, capsule, emulsion, and the like. The egg-laying rate-improving agent of the present invention can be produced by mixing unheated cashew nut shell liquid, heated cashew nut shell liquid, anacardic acid, cardanol, and/or cardol, and any optional components, as necessary, for formulation. In addition, according to the dosage form, cashew nut shell, pulverized/crushed cashew nut shell, or cashew nut testa, which contains cashew nut shell liquid, may be mixed directly with any other components to produce the egg-laying rate-improving agent of the present invention. Furthermore, cashew nut shell itself, pulverized/crushed cashew nut shell itself, or cashew nut testa itself, not mixed with any other components, may be used as a feed additive, and further as a feed.

The egg-laying rate-improving agent of the present invention may be produced as a powder with silica, such as silica with an average diameter of not less than 150 μm, on which unheated cashew nut shell liquid, heated cashew nut shell liquid, anacardic acid, cardanol, and/or cardol are/is adsorbed or contained. Such a silica formulation is described in, for example, WO2009/151048.

In regard to the egg-laying rate-improving agent of the present invention, unheated cashew nut shell liquid, heated cashew nut shell liquid, anacardic acid, cardanol, and/or cardol may be mixed appropriately with calcium carbonate, diatom earth, bentonite, montmorillonite, zeolite, perlite, acid clay, activated clay, and/or hydrated silica to produce a feed additive. Such oil absorbing agents are described in, for example, WO2011/013592.

The egg-laying rate-improving agent of the present invention may be mixed with other feed components used in food for poultry and supplemental food for poultry (hereinafter referred to as feed) to produce a feed. The type of the feed and the components other than cashew nut shell liquid are not particularly limited. The feed is for poultry such as chicken and quails.

The feed additive can be added directly to and mixed with feed components to produce the feed of the present invention. At that time, in cases where the feed additive either in powder or solid is used, the feed additive may be transformed to either liquid or gel state for ease of mixing. In this case, water, vegetable oil such as soybean oil, rapeseed oil, corn oil and the like, liquid animal oil, or water-soluble high molecular compounds such as polyvinyl alcohol, polyvinylpyrrolidone, and polyacrylic acid may be used as a liquid carrier. Moreover, water soluble polysaccharides such as alginic acid, sodium alginate, xanthan gum, sodium caseinate, gum arabic, guar gum, tamarind seed polysaccharides and the like are also preferably combined to keep the homogeneity of cashew nut shell liquid in the feed.

The feed of the present invention may comprise sugars (lactose, trehalose and the like), maize, milo, wheat bran, rice bran, defatted bran, dried bran, steam-rolled barley, steam-rolled corn, soybean cake, corn flour, rice flour, soybean flour and the like. The concentration of these components in the feed is preferably from 1 to 90% by mass, more preferably from 5 to 75% by mass and further preferably from 10 to 50% by mass.

The feed of the present invention may additionally comprise optional components, such as ingredients effective in growth promotion in egg-laying chickens, quails, or broiler breeders, nutritional supplements, ingredients to enhance storage stability, and the like. Examples of such optional components include probiotics such as *Enterococcus* spp., *Bacillus* spp., *Bifidobacterium* spp.; enzymes such as amylase and lipase; vitamins such as L-ascorbic acid, choline chloride, inositol, and folic acid; minerals such as potassium chloride, ferric citrate, magnesium oxide, and phosphoric acid salts; amino acids such as D,L-alanine, D,L-methionine, and L-lysine hydrochloride; organic acids such as fumaric acid, butyric acid, lactic acid, and acetic acid, and salts thereof; antioxidants such as ethoxyquin and dibutyl hydroxy toluene; fungicides such as calcium propionate; thickeners such as carboxymethyl cellulose (CMC), sodium caseinate, and sodium polyacrylate; emulsifiers such as glycerin fatty acid esters and sorbitan fatty acid esters; pigments such as asthaxanthin and canthaxanthin; and flavors such as various esters, ethers, and ketones.

The feed of the present invention is suitable for rearing egg-laying hens, quails, or broiler breeders. The amount of feed to be given can be appropriately adjusted depending on the breed of hens or quails, body weight, age, sex, health conditions, components of the feed, and the like, in which the unheated cashew nut shell liquid, heated cashew nut shell liquid, anacardic acid, cardanol, and/or cardol contained in the feed is provided in a ratio of preferably 0.001 to 100 grams per chicken per day, more preferably 0.001 to 50 grams per chicken per day and further preferably 0.001 to 10 grams per chicken per day. Routine methods can be used as a feeding method and a rearing method, depending on the breed of chickens or quails. The examples of the present invention will be described below but the present invention will not be limited thereto.

EXAMPLES

Production Example 1

Cashew nut shell liquid (CNSL) was purchased from Thao Nguyen Co., Ltd. The composition of the CNSL was determined by the method below. That is, a HPLC system (Waters 600, Nihon Waters K.K.), a detector (Waters 490E, Nihon Waters K.K.), a printer (Chromatopac C-R6A, Shimadzu Corp.) and a column (SUPELCOSIL LC18, Supelco) were used. A solvent of acetonitrile/water/acetic acid (80:20:1, vol/vol/vol) was used and the flow rate was 2 ml/min. Detection was performed by absorbance at 280 nm. The cashew nut shell liquid contained 65.7% by mass of anacardic acid, 5.1% by mass of cardanol and 23.5% by mass of cardol.

Example 1

When the CNSL was mixed with a feed for induced molting, which is characterized by being a low energy-low protein diet, at a final concentration of 100 ppm and fed during 30 days in the period from 65 to 67 weeks of age in which induced molting was implemented, a considerably decreased death rate during molting (a decrease of 45%) and an increased duration in days of egg production phase after molting (from 133 to 147 days; an increase of 11%) as compared with a control group were observed in Julia-Lite (about 20,000 chickens/group, white egg-laying breed). The results are shown in Tables 1 to 3.

TABLE 1

| | Feeding group | | | | | |
|---|---|---|---|---|---|---|
| | Body weight (g) | No. of hens | No. of eggs | Egg-laying rate (%) | Weight loss rate (%) | Death rate (%) |
| The day before molting | 1,887 | 19,465 | 16,692 | 85.75 | — | — |
| 5th day in molting | 1,629 | 19,424 | 12,747 | 65.63 | 13.67 | 0.21 |
| 10th day in molting | 1,488 | 19,260 | 8,239 | 42.78 | 21.14 | 1.05 |
| 15th day in molting | 1,386 | 19,203 | 170 | 0.89 | 26.55 | 1.35 |
| 20th day in molting | 1,344 | 19,185 | 8 | 0.04 | 28.78 | 1.44 |
| 25th day in molting | 1,443 | 19,167 | 50 | 0.26 | 23.53 | 1.53 |
| 30th day in molting | 1,548 | 19,161 | 587 | 3.06 | 17.97 | 1.56 |

TABLE 2

| | Control group | | | | | |
|---|---|---|---|---|---|---|
| | Body weight (g) | No. of hens | No. of eggs | Egg-laying rate (%) | Weight loss rate (%) | Death rate (%) |
| The day before molting | 1,739 | 19,514 | 16,522 | 84.67 | — | — |
| 5th day in molting | 1,531 | 19,425 | 13,284 | 68.39 | 11.96 | 0.46 |
| 10th day in molting | 1,394 | 19,230 | 6,250 | 32.50 | 19.84 | 1.46 |
| 15th day in molting | 1,302 | 19,138 | 292 | 1.53 | 25.13 | 1.93 |
| 20th day in molting | 1,247 | 19,022 | 17 | 0.09 | 28.29 | 2.52 |
| 25th day in molting | 1,317 | 18,967 | 15 | 0.08 | 24.27 | 2.80 |
| 30th day in molting | 1,373 | 18,958 | 292 | 1.54 | 21.05 | 2.85 |

TABLE 3

| | Feeding group | | | | | Control group | | | | |
|---|---|---|---|---|---|---|---|---|---|---|
| | No. of hens | Survival rate (%) | No. of eggs | Egg-laying rate (%) | Cumulative feed conversion rate (%) | No. of hens | Survival rate (%) | No. of eggs | Egg-laying rate (%) | Cumulative feed conversion rate (%) |
| 1 week after molting | 19,159 | 94.1 | 2,466 | 12.87 | 1.99 | 18,944 | 92.2 | 3,400 | 17.95 | 2.10 |
| 2 weeks after molting | 19,149 | 94.1 | 9,944 | 51.93 | 2.01 | 18,934 | 92.2 | 8,880 | 46.90 | 2.12 |
| 3 weeks after molting | 19,133 | 94.0 | 15,354 | 80.25 | 2.01 | 18,924 | 92.1 | 13,739 | 72.60 | 2.13 |

TABLE 3-continued

| | Feeding group | | | | Control group | | | | |
|---|---|---|---|---|---|---|---|---|---|
| | No. of hens | Survival rate (%) | No. of eggs | Egg-laying rate (%) | Cumulative feed conversion rate (%) | No. of hens | Survival rate (%) | No. of eggs | Egg-laying rate (%) | Cumulative feed conversion rate (%) |
| 4 weeks after molting | 19,118 | 93.9 | 17,459 | 91.32 | 2.01 | 18,910 | 92.1 | 17,153 | 90.71 | 2.12 |
| 5 weeks after molting | 19,099 | 93.8 | 17,638 | 92.35 | 2.01 | 18,889 | 92.0 | 17,314 | 91.66 | 2.12 |
| 6 weeks after molting | 19,071 | 93.7 | 17,559 | 92.07 | 2.01 | 18,879 | 91.9 | 17,559 | 93.01 | 2.12 |
| 7 weeks after molting | 19,051 | 93.6 | 17,590 | 92.33 | 2.01 | 18,864 | 91.8 | 17,453 | 92.52 | 2.11 |
| 8 weeks after molting | 19,031 | 93.5 | 17,627 | 92.62 | 2.01 | 18,846 | 91.7 | 17,385 | 92.25 | 2.11 |
| 9 weeks after molting | 19,016 | 93.4 | 17,466 | 91.85 | 2.01 | 18,828 | 91.7 | 17,363 | 92.22 | 2.11 |
| 10 weeks after molting | 18,998 | 93.3 | 17,355 | 91.35 | 2.01 | 18,807 | 91.6 | 17,269 | 91.82 | 2.10 |
| 11 weeks after molting | 18,982 | 93.2 | 17,351 | 91.41 | 2.01 | 18,785 | 91.5 | 17,158 | 91.34 | 2.10 |
| 12 weeks after molting | 18,965 | 93.2 | 17,152 | 90.44 | 2.01 | 18,764 | 91.3 | 17,222 | 91.78 | 2.10 |
| 13 weeks after molting | 18,945 | 93.1 | 17,088 | 90.20 | 2.01 | 18,743 | 91.2 | 17,137 | 91.43 | 2.09 |
| 14 weeks after molting | 18,918 | 92.9 | 17,213 | 90.99 | 2.00 | 18,718 | 91.1 | 17,075 | 91.22 | 2.09 |
| 15 weeks after molting | 18,899 | 92.8 | 17,327 | 91.68 | 2.00 | 18,688 | 91.0 | 16,969 | 90.80 | 2.09 |
| 16 weeks after molting | 18,880 | 92.7 | 16,832 | 89.15 | 2.00 | 18,669 | 90.9 | 16,907 | 90.56 | 2.08 |
| 17 weeks after molting | 18,859 | 92.6 | 17,313 | 91.80 | 2.00 | 18,635 | 90.7 | 16,904 | 90.71 | 2.08 |
| 18 weeks after molting | 18,837 | 92.5 | 17,181 | 91.21 | 1.99 | 18,604 | 90.6 | 16,695 | 89.74 | 2.08 |
| 19 weeks after molting | 18,810 | 92.4 | 17,042 | 90.60 | 1.99 | 18,574 | 90.4 | 16,735 | 90.10 | 2.07 |
| 20 weeks after molting | 18,778 | 92.2 | 17,052 | 90.81 | 1.99 | 18,535 | 90.2 | 16,572 | 89.41 | 2.07 |
| 21 weeks after molting | 18,753 | 92.1 | 17,242 | 91.94 | 1.99 | 18,508 | 90.1 | 16,311 | 88.13 | 2.07 |
| 22 weeks after molting | 18,719 | 91.9 | 16,546 | 88.39 | 1.98 | 18,479 | 90.0 | 16,311 | 88.27 | 2.06 |
| 23 weeks after molting | 18,692 | 91.8 | 16,227 | 86.81 | 1.98 | 18,444 | 89.8 | 16,161 | 87.62 | 2.06 |
| 24 weeks after molting | 18,689 | 91.8 | 15,575 | 83.34 | 1.98 | 18,436 | 89.8 | 15,949 | 86.51 | 2.06 |
| 25 weeks after molting | 18,683 | 91.8 | 15,570 | 83.34 | 1.98 | 18,388 | 89.5 | 16,474 | 89.59 | 2.06 |
| 26 weeks after molting | 18,677 | 91.7 | 15,052 | 80.59 | 1.98 | 18,353 | 89.3 | 15,760 | 85.87 | 2.05 |
| 27 weeks after molting | 18,669 | 91.7 | 15,996 | 85.68 | 1.98 | 18,323 | 89.2 | 15,677 | 85.56 | 2.05 |
| 28 weeks after molting | 18,667 | 91.7 | 15,611 | 83.63 | 1.98 | 18,286 | 89.0 | 15,507 | 84.80 | 2.05 |
| 29 weeks after molting | 18,665 | 91.7 | 15,339 | 82.18 | 1.98 | 18,245 | 88.8 | 15,211 | 83.37 | 2.05 |
| 30 weeks after molting | 18,663 | 91.7 | 15,453 | 82.80 | 1.98 | 18,212 | 88.7 | 15,269 | 83.84 | 2.05 |
| 31 weeks after molting | 18,659 | 91.6 | 15,362 | 82.33 | 1.98 | 18,177 | 88.5 | 13,969 | 76.85 | 2.05 |
| 32 weeks after molting | 18,608 | 90.6 | 14,864 | 79.88 | 1.98 | 18,138 | 88.3 | 14,804 | 81.62 | 2.05 |
| 33 weeks after molting | 18,405 | 90.4 | 14,949 | 81.22 | 1.99 | 18,089 | 88.1 | 14,562 | 80.50 | 2.05 |
| 34 weeks after | 18,343 | 90.1 | 14,451 | 78.78 | 1.99 | 18,057 | 87.2 | 14,355 | 79.50 | 2.05 |

As seen in Tables 1 and 2, the death rate during the molting process was 1.56%, while it was 2.85% in the control group, indicating an improvement of about 45% by comparison. Moreover, as seen in Table 3, an egg-laying rate of 90% after molting was maintained for 147 days after the molting, while it was maintained for 133 days in the control group, indicating an increase of about 11% by comparison.

Example 2

The CNSL was mixed with a feed for adult chickens at a final concentration of 100 ppm and fed to adult hens during 30 days in the period from 26 to 29 weeks of age (Example), which corresponds to the period from the introduction of adult hens to the peak egg-laying phase. The hen breed used was Julia (81,000 hens/group, white egg-laying breed) and adult hens which had been fed with the CNSL for 3 weeks (from 30 to 32 weeks of age) were used as a control group (Comparative Example), in consideration of varying egg-laying rates depending on the weekly age of chickens. Consequently, an improved hen-day egg production (from 87.0 to 91.1% on average for the period: an improvement of 5%), hen-house egg production (from 86.5% to 90.8%: an improvement of 5%) and a decreased number of dead chickens per day (from 17 to 6 chickens on average: a decrease of 65%) were observed in the CNSL-feeding period, as compared with the control period. The egg weight in both periods changed almost similarly to the corresponding parameter in commercial hens. The results are shown in Tables 4 and 5. Feeding design, lighting control and the like were implemented according to routine procedures of the participating farm.

TABLE 4

|  | Age in weeks | No. of dead hens/day | Survival rate | No. of of eggs produced | Hen-day egg production | Hen-house egg production | Daily egg output | Total egg weight |
|---|---|---|---|---|---|---|---|---|
| Feeding period | 26 | 7 | 99.8 | 71,968 | 89.05 | 88.87 | 51.01 | 4,123 |
|  | 27 | 8 | 99.7 | 73,072 | 90.47 | 90.23 | 51.65 | 4,172 |
|  | 28 | 5 | 99.7 | 73,296 | 90.80 | 90.51 | 53.30 | 4,302 |
|  | 29 | 5 | 99.6 | 75,803 | 93.96 | 93.61 | 54.93 | 4,431 |
| Control period | 30 | 8 | 99.5 | 71,717 | 88.97 | 88.56 | 52.58 | 4,238 |
|  | 31 | 15 | 99.4 | 69,479 | 86.30 | 85.80 | 51.69 | 4,162 |
|  | 32 | 27 | 99.2 | 68,962 | 85.85 | 85.16 | 51.05 | 4,101 |

TABLE 5

|  | Age in weeks | Average egg weight in the tested groups (g) | Average egg weight according to the parameter in (g) commercial chickens |
|---|---|---|---|
| Feeding period | 26 | 57.29 | 57.60 |
|  | 27 | 57.09 | 58.30 |
|  | 28 | 58.69 | 59.00 |
|  | 29 | 58.45 | 59.50 |
| Control period | 30 | 59.09 | 60.00 |
|  | 31 | 59.90 | 60.50 |
|  | 32 | 59.47 | 61.00 |

As seen in Table 4, an improved hen-day egg production and a decreased number of dead hens due to the feeding of the CNSL were observed. The stage during which the egg production peaks corresponds to the period in which egg-laying hens show their highest productivity; therefore, maintaining a high survival rate and simultaneously increasing the egg-laying rate in this stage results in a considerably increased productivity of the group of hens. Furthermore, as shown in Table 5, even though the egg-laying rate was increased by the feeding of the CNSL, the average egg weight was almost similar to the corresponding parameter in commercial Julia chickens and deterioration in the quality of eggs in parallel with increase in egg-laying rate was not induced. Although actual values are not shown, the incidence of abnormal eggs such as broken egg was not different from the normal value. That is, the feeding of the CNSL was indicated to enhance the performance of egg-laying hens in three aspects: increase in egg-laying rate, decrease in number of dead hens, and increase in the quality of eggs.

Example 3

The CNSL was mixed with a feed for adult chickens at a final concentration of 50 ppm and fed to a group of adult chickens, to which feeding had started in March, during 67 days in the period from 17 to 26 weeks of age, which corresponds to the period from the introduction of adult chickens to the peak egg-laying phase. The chicken breed used was Babcock B400 (50,000 chickens/group, white egg-laying breed). Average values derived from two groups of adult chickens (100,000 chickens: fed with a CNSL-free feed), to which feeding had started on the same farm in March one year ago and in March two years ago, respectively, were used as a control group. Consequently, a decreased duration in days until 50% of chickens in a group reach the egg-laying phase (from 150 days to 143 days: a decrease of 5%), an improved hen-day egg production (from 41.6% to 50.2% on average for the period: an improvement of 21%), and an increased number of eggs produced per hen house (from 29.3 to 35.4 eggs: an increase of 21%) were observed in the CNSL-feeding group, as compared with the control group. The survival rate was lower in the feeding group until 26 weeks of age, but it was increased later to an almost equal value by 28 weeks of age. The results are shown in Table 6. Feeding design, lighting control and the like were implemented according to routine procedures of the participating farm.

TABLE 6

| Age (wks) | Survival rate Feeding | Survival rate Control | Cumulative No. of dead hens Feeding | Cumulative No. of dead hens Control | HH No. of eggs Feeding | HH No. of eggs Control | No. of eggs/day Feeding | No. of eggs/day Control | Hen-day egg production Feeding | Hen-day egg production Control |
|---|---|---|---|---|---|---|---|---|---|---|
| 17 | 99.9 | 100 | 50 | 0 | 0.0 | 0.0 | — | — | 0 | 0 |
| 18 | 99.9 | 100 | 50 | 0 | 0.1 | 0.0 | 714 | — | 1.4 | 0.0 |
| 19 | 99.8 | 99.9 | 100 | 50 | 0.7 | 0.1 | 4,286 | 714 | 8.6 | 1.4 |
| 20 | 99.6 | 99.9 | 200 | 50 | 2.5 | 1.0 | 12,857 | 6,429 | 25.6 | 12.8 |
| 21 | 99.5 | 99.7 | 250 | 150 | 6.1 | 3.2 | 25,714 | 15,714 | 51.2 | 31.3 |
| 22 | 99.4 | 99.6 | 300 | 200 | 11.2 | 6.7 | 36,429 | 25,000 | 72.4 | 49.8 |
| 23 | 99.3 | 99.5 | 350 | 250 | 16.8 | 11.3 | 40,000 | 32,857 | 79.4 | 65.4 |
| 24 | 99.3 | 99.5 | 350 | 250 | 22.8 | 15.9 | 42,857 | 40,000 | 85.1 | 79.6 |
| 25 | 99.2 | 99.4 | 400 | 300 | 29.2 | 23.0 | 45,714 | 43,571 | 90.7 | 86.6 |
| 26 | 99.1 | 99.3 | 450 | 350 | 39.4 | 29.3 | 44,286 | 45,000 | 87.8 | 89.4 |

As shown in Table 6, a decreased duration in days until 50% of chickens in a group reach the egg-laying phase and an improved hen-day egg production due to the addition of the CNSL at a concentration of 50 ppm were observed, and an increased number of eggs produced per hen house were consequently obtained. For the purpose of increasing the productivity per egg-laying hen and the productivity per hen house, it is very important that introduced adult hens are allowed to enter smoothly into the egg-laying phase and to increase their egg-laying rate. Thus, CNSL was indicated to have high industrial effectiveness.

Production Example 2

Heated CNSL was obtained by heating the CNSL obtained in Production Example 1 at 100° C. When the composition was determined by the same method as described above, it contained no anacardic acid, 72.9% by mass of cardanol and 19.7% by mass of cardol.

Example 4

Heated CNSL produced by the same method in Production Example 2 was mixed with a feed for adult chickens at a final concentration of 50 ppm and fed to adult hens during 28 days in the period of 18 to 21 weeks of age, following the introduction of the adult hens. The chicken breed used was Babcock B400 (50,000 chickens/group, white egg-laying breed). Adult hens (fed with a CNSL-free feed) grown in another hen house in the same time period were used as a control group. Consequently, an increased number of eggs produced per hen house (from 4.2 to 4.7 eggs; an increase of 12%) and an improved hen-day egg production (from 42.7% to 45.6% at a point of 21 weeks of age: an improvement of 7%) were observed in heated CNSL-feeding group, as compared with the control group. The survival rate was almost comparable between the groups. The results are shown in Table 7. Feeding design, lighting control and the like were implemented according to routine procedures of the participating farm.

As seen also in Table 7, an improved egg-laying rate and a consequent increased number of eggs produced per hen house were also observed due to the heated CNSL formulation. In particular, a good number of eggs produced per day were obtained in early weeks of age in the feeding group.

INDUSTRIAL APPLICABILITY

The egg-laying rate-improving agent of the present invention and the feed comprising the same are useful in the field of egg-laying poultry.

The invention claimed is:

1. A method for egg production, the method comprising egg-laying hens an effective amount of a feed comprising an effective amount of unheated cashew nut shell liquid (CNSL) which comprises from 55 to 80 mass % of anacardic acid, from 5 to 20 mass % of cardanol, and from 5 to 30 mass % of cardol, or heated cashew nut shell liquid which comprises from 0 to 10 mass % of anacardic acid, from 55 to 80 mass % of cardanol, and from 5 to 30 mass % of cardol,
   wherein the egg-laying hens are female birds of chickens or quails,
   wherein an egg-laying rate of not lower than 90% is maintained for 90 days or longer,
   wherein layer performance is enhanced by increasing or maintaining quality of eggs,
   wherein the feed is fed during a peak egg-laying phase or during a molting process of the female birds, and
   wherein a number of dead birds per week during the peak egg-laying phase is less than 0.1% of a number of total female birds.

2. The method of claim 1, comprising feeding the layers, wherein the laying are subjected to forced molting or induced molting.

TABLE 7

| (wks) | Survival rate Feeding | Survival rate Control | Cumulative No. of dead hens Feeding | Cumulative No. of dead hens Control | HH No. of eggs Feeding | HH No. of eggs Control | No. of eggs/day Feeding | No. of eggs/day Control | Hen-day egg production Feeding | Hen-day egg production Control |
|---|---|---|---|---|---|---|---|---|---|---|
| 18 | 100 | 100 | 0 | 0 | 0.1 | 0 | 714 | — | 1.4 | 0.0 |
| 19 | 99.9 | 99.9 | 50 | 50 | 0.3 | 0.1 | 1,429 | 714 | 2.9 | 1.4 |
| 20 | 99.9 | 99.9 | 50 | 50 | 1.5 | 1.2 | 8,571 | 7,857 | 17.1 | 15.7 |
| 21 | 99.8 | 99.7 | 100 | 150 | 4.7 | 4.2 | 22,857 | 21,429 | 45.6 | 42.7 |

3. The method of claim 2, wherein a death rate during the forced molting or induced molting is not more than 2%.

4. The method according to claim 1, wherein the feed comprises unheated cashew nut shell liquid, or heated cashew nut shell liquid at a final concentration of from 50 to 100 ppm.

5. The method according to claim 1, wherein the feed is fed during a molting process of the female birds, and wherein the feed is a low energy-low protein diet.

6. The method according to claim 5, wherein the feed is fed during a period from 65 to 67 weeks of age of the female birds.

7. The method according to claim 1, wherein the feed is fed around the peak egg-laying phase in a period from 17 to 29 weeks of age of the female birds.

\* \* \* \* \*

UNITED STATES PATENT AND TRADEMARK OFFICE
CERTIFICATE OF CORRECTION

PATENT NO. : 10,953,057 B2
APPLICATION NO. : 15/547238
DATED : March 23, 2021
INVENTOR(S) : Eiji Iwamoto et al.

Page 1 of 1

It is certified that error appears in the above-identified patent and that said Letters Patent is hereby corrected as shown below:

In the Claims

Column 16, Line 32, Claim 1, "egg-laying" should read -- feeding egg-laying --.

Signed and Sealed this
Tenth Day of August, 2021

Drew Hirshfeld
*Performing the Functions and Duties of the
Under Secretary of Commerce for Intellectual Property and
Director of the United States Patent and Trademark Office*